United States Patent
Cummins et al.

(10) Patent No.: US 6,506,377 B2
(45) Date of Patent: Jan. 14, 2003

(54) INTERFERON-ALPHA MEDIATED UPREGULATION OF AQUAPORIN EXPRESSION

(75) Inventors: Joseph M. Cummins, Amarillo, TX (US); J. Kelly Smith, Johnson City, TN (US)

(73) Assignees: Amarillo Biosciences, Inc., Amarillo, TX (US); East Tennessee State University, Johnson City, TN (US)

( * ) Notice: Subject to any disclaimer, the term of this patent is extended or adjusted under 35 U.S.C. 154(b) by 0 days.

(21) Appl. No.: 09/964,792

(22) Filed: Sep. 27, 2001

(65) Prior Publication Data

US 2002/0037273 A1 Mar. 28, 2002

Related U.S. Application Data

(62) Division of application No. 09/448,698, filed on Nov. 24, 1999, now abandoned.
(60) Provisional application No. 60/109,791, filed on Nov. 25, 1998.

(51) Int. Cl.[7] .......................... A61K 38/21; A61K 38/16
(52) U.S. Cl. .................... 424/85.7; 424/85.4; 424/85.1; 514/8; 514/851; 514/826
(58) Field of Search ............................... 424/85.7, 85.4, 424/85.1; 514/8, 851, 826

(56) References Cited

U.S. PATENT DOCUMENTS 5,863,530 A * 1/1999 Gillies et al. ............... 424/85.7

OTHER PUBLICATIONS

Li et al. The Journal of Immunology. vol. 157, No. 8, pp. 3216–3219. Oct. 1996.*

Ferraccioli et al. Clinical Exp. Rhheumatology (Italy). vol. 14 No. 4, pp. 367–371, (1996).*

"Localization and expression of AQP5 in cornea, serous salivary glands, and pulmonary epithelial cells," H. Funaki, et al., The American Physiological Society, 0363–6143/98, C1151–C1157 (1998).

"Aquaporins in complex tissues. I. Development patterns in respiratory and glandular tissues of rat," L. King et al., The American Physiological Society, 0363–6143/97, C1541–C1548 (1997).

"Aquaporins in complex tissues. II. Subcellular distribution in respiratory and glansnular tissues of rat," L. King et al., The American Physiological Society, 0363–6143/97, C1549–C1561 (1997).

"Genetics of airway responsiveness in the inbred mouse," G. De Sanctis, et al., PubMed Abstract, PMID 9176291.

* cited by examiner

*Primary Examiner*—Prema Mertz
*Assistant Examiner*—Fozia Hamud
(74) *Attorney, Agent, or Firm*—Barnes & Thornburg

(57) ABSTRACT

A method for enhancing the expression of aquaporin proteins by contacting aquaporin producing cells with interferon-α is described. The method enables treatment of patients afflicted with disease states characterized by xerosis.

7 Claims, 3 Drawing Sheets

INTERFERON-ALPHA MEDIATED UPREGULATION OF AQUAPORIN EXPRESSION

CROSS REFERENCE TO RELATED APPLICATIONS

This application is a divisional of U.S. application Ser. No.09/448,698 filed Nov. 24, 1999 (now abandoned) which claims priority under 35 U.S.C. § 119 (e) to U.S. Provisional Application No. 60/109,791, filed Nov. 25, 1998, which is expressly incorporated by reference herein.

FIELD OF THE INVENTION

This invention relates to a method for relieving xerotic symptoms (abnormal dryness) by up regulating aquaporin production in cells. More particularly, the present invention is directed to a method. for enhancing expression of aquaporin proteins in aquaporin producing cells of a warm-blooded vertebrate by contacting said cells with an effective amount of interferon-alpha (IFN-α).

BACKGROUND/SUMMARY OF THE INVENTION

Aquaporin proteins are members of the MIP (Major Intrinsic Protein) family. Such proteins occur in many different organisms, such as yeasts, plants, bacteria, insects, and mammals, including humans. The member proteins of the MIP family comprise approximately 250–290 amino acid units and the sequences differ mainly at their N and C termini. All MIPs are found in vivo as intrinsic membrane proteins (i.e, they sequester with the membrane fraction in centrifugations of cell suspensions, etc.). Current studies indicate that MIPs, including aquaporins, are membrane-bound channel proteins.

Aquaporins are large and highly conserved membrane proteins that function as highly selective water channels. After being formed within the cell, aquaporin lodges in the plasma membrane, with six transmembrane regions looping through the membrane bilayer and forming the protein channel through which water passes freely.

Aquaporins move water using a passive process driven by the osmotic gradient across the cell membrane. To date, six mammalian aquaporins, numbered 0–5, have been identified. For example, Aquaporin 5 (AQ-5) is abundant in salivary and lacrimal glands, where it is thought to contribute to saliva and tear production. AQ-5 is also expressed in the adult lung, where it is believed to 6 be at least partially responsible for respiratory transpiration.

Aquaporins play a central role in water homeostasis in both plants and animals, as indicated by the localization of aquaporins to the moist surface tissues of the alveoli, the kidney tubules, the choroid plexus of the brain (where cerebrospinal fluid is produced), the ciliary epithelium of the eye (where aqueous humor is formed) and in salivary and lacrimal glands. Physiological studies further illustrate the importance of aquaporins to the maintenance of proper water homeostasis. For example, Xu et al. demonstrated that Aquaporin 2 is upregulated in kidney collecting tubules during congestive heart failure, thereby exacerbating the disease by causing increased water retention. *J. Clin. Invest.,* 99(7): 1500–5(1997). Due to their important role in water regulation of biological systems, aquaporins are believed to be potential targets for therapeutic intervention in disease states involving symptoms of improper water homeostasis.

The present invention is based in part on the discovery that interferon upregulates expression of aquaporin proteins, and further that administration of interferon in vivo for contact with relevant cell populations is beneficial in treating disease states wherein water homeostasis is compromised.

"Interferon" is a term generically describing a group of vertebrate glycoproteins and proteins which are known to have antiviral, antiproliferative and immunomodulatory activity. In the early years of interferon research, an international committee was assembled to devise a system for orderly nomenclature of interferons and defined "interferon" as follows: "To qualify as an interferon a factor must be a protein which exerts virus non-specific, antiviral activity at least in homologous cells through cellular metabolic process involving synthesis of both RNA and protein." *Journal of Interferon Research,* 1, pp. vi (1980). "Interferon" as used herein in describing the present invention shall be deemed to have that definition and shall contemplate such proteins, including glycoproteins, regardless of their source or method of preparation or isolation.

Interferons have generally been named in terms of the species of animal cells producing the substance, the type of cell involved (e.g., leukocyte/lymphoblastoid or fibroblast) and, occasionally, the type of inducing material responsible for interferon production. The designations alpha (α), beta (β) and gamma(γ) have been used to correspond to the previous designations of leukocyte, fibroblast, and immune interferons, respectively. Alpha and beta interferons are usually acid-stable and correspond to what have been called Type I interferons; gamma interferons are usually acid-labile and correspond to what have been called Type II interferons. More recently, interferon tau has been described as an interferon-alpha related Type I interferon produced by bovine and ovine trophoblasts.

Interferon of human and murine origin is quantified in the art in terms of International Units (IU). Interferons of other than human or murine origin can be used in accordance with this invention. In that presently accepted practices may not extend the use of "International Units" to quantify non-human and non-murine interferons, it shall be understood that administration of amounts of non-human/non-murine interferons having the same efficacy as the quantities (IU's) of human interferon specified in this description are within the scope of the present invention.

In accordance with this invention, interferon-alpha is administered to a patient suffering from a disease state characterized generally by conditions of dryness of mucosal tissue. For the purpose of the present invention, appropriate IFN-α treatment dosages range from about 0.1 IU/lb to about 100 IU/lb of patient body weight, more typically about 0.5 to about 10 IU/lb of patient body weight. Thus, unit dosage forms for human use typically comprise about 5 IU to about 2500 IU of interferon-α, more typically about 10 IU to about 300 IU of interferon-α, in combination with a pharmaceutically acceptable carrier therefor. Dosage forms for treatment in accordance with this invention can be in solid, liquid, aerosol, ointment or cream formulation and are typically administered from one to four times daily until the xerotic condition being treated is alleviated. Chronic administration may be required for sustained benefit. Generally speaking, the dosage forms are administered in a disease state-dependent manner, including particularly administration topically, bucally/sublingually, by oral ingestion or by inhalation.

BRIEF DESCRIPTION OF THE DRAWINGS

The various advantages of the present invention will become apparent to one skilled in the art by reading the following specification and by referencing the following drawings in which.

DETAILED DESCRIPTION OF THE INVENTION

Figure 1:
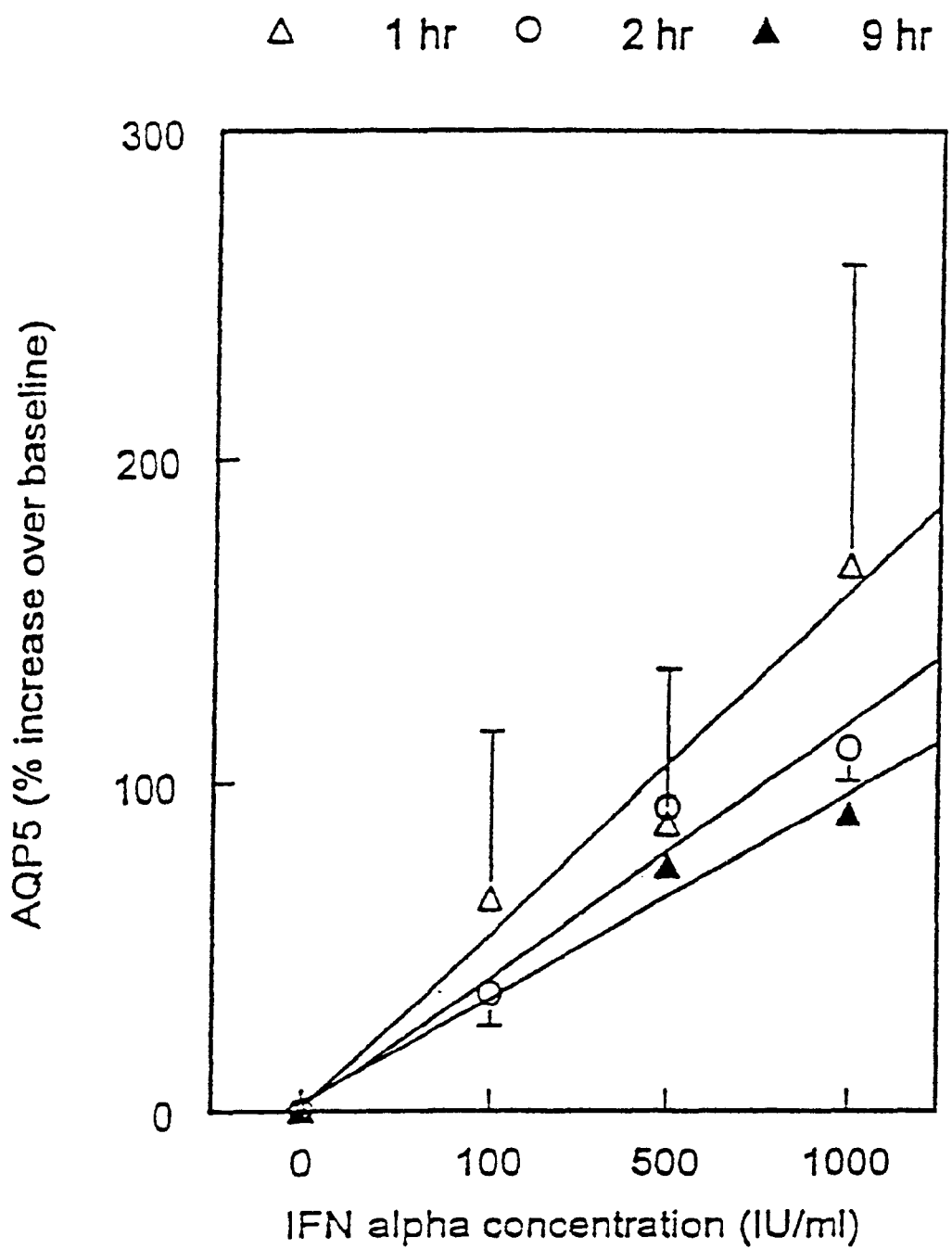
FIG. 1 is a graph showing the relationship between aquaporin-5 transcription and increasing concentrations of interferon-alpha.

The present invention relates to a method for enhancing expression of an aquaporin protein in aquaporin producing cells of a warm-blooded vertebrate. The present invention enables use of an effective amount of IFN-α to treat certain pathological states that produce mouth dryness (xerostomia), alterations of lacrimation (xerophthalmia) and/or abnormal accumulation of mucous in the lungs, as well as other xerotic (i.e., abnormally dry) physiological conditions.

The present method involves the administration of IFN-α for contacting mucosal and/or glandular tissues involved in water homeostasis. Generally, such tissues comprise secretory cells that serve. to lubricate surrounding tissue or facilitate the movement of water through surrounding tissue. In the present method, patients afflicted with xerotic conditions are treated with IFN-α to alleviate abnormal dryness of such mucosal tissues. Typical tissues to be targeted for treatment using the present method include the oral mucosa, the nasopharyngeal mucosa, salivary glands, the conjunctiva of the eye, lacrimal glands, vaginal mucosa and/or the lungs.

One embodiment of the method comprises the step of contacting aquaporin producing cells with an amount of IFN-α effective to upregulate aquaporin expression in said cells. Such contact can be accomplished through administration of any suitable dosage form, including (but not limited to) aqueous solution, lozenges, tablets, capsules, topical creams, ointments or suppositories.

In another embodiment of the present method, IFN-α is administered to a warm-blooded vertebrate having a disease state characterized by diminished function of cells responsible for tear production or lacrimation. In this embodiment of the invention, INF-α in an amount effective to upregulate aquaporin protein production and thereby enhance lacrimation may be administered orally, buccally, or topically to the conjunctiva or lacrimal gland of said vertebrate.

Administration of IFN-α is useful in accordance with this invention for treatment of keratoconjunctivitis sicca (KCS). KCS is a common problem in dogs; there is an approximately 2% prevalence in the canine population in the United States. There are numerous causes for KCS including drugs (i.e., sulfa drugs, parasympatholytic drugs), trauma, chronic conjunctivitis, and infections (e.g., viral canine distemper) etc. The most common cause in dogs is spontaneous, immune-mediated KCS. In immune-mediated KCS, the lacrimal glands become progressively infiltrated with mononuclear cells. Tissue destruction occurs and eventually fibrosis replaces the lacrimal tissue. KCS is most common in middle-aged (i.e., 6–10 year old) neutered female dogs and in specific breeds of dogs (e.g., West Highland white terriers, bulldogs, cocker spaniels, etc). Without treatment, naturally-occurring, immune-mediated KCS in dogs is a progressive, chronic condition. Lacrimation levels in these dogs remain low and the clinical signs of KCS do not spontaneously improve.

Previously, treatment for canine KCS has consisted of frequent use of topical artificial tears, topical and/or systemic antibiotics to treat secondary bacterial infections, topical or oral tear stimulants, (e.g., pilocarpine), and topical surface wetting agents such as sodium hyaluronate. These treatments are successful in many cases of KCS, especially when the condition is recognized early in the course of disease. Unfortunately, many cases of KCS are not presented for evaluation or not diagnosed until late in the clinical course when signs are chronic and the condition is poorly responsive to medication.

Approximately ten years ago, topical cyclosporin A (either a 0.2% ointment, or 1 or 2% drop in oil) was introduced as a treatment for canine KCS and has been beneficial in >75% of dogs with canine KCS. in many cases, topical cyclosporin A reduces corneal and conjunctival inflammation and cellular infiltrates into the lacrimal gland thereby allowing the lacrimal gland to resume tear production. Since its introduction, topical cyclosporin A has become the treatment of choice for treatment of immune-mediated KCS in dogs; however, this drug does have its disadvantages. Cyclosporin A therapy is expensive and, because treatment is required for the life of the patient, represents a substantial financial commitment for dog owners. Proper treatment requires topical ocular application 2–3 times per day. Side effects from the cyclosporin A and vehicle have been reported and significant systemic absorption and decrease of lymphocyte function have been seen, especially in smaller dogs (i.e., less than 10 kg). Cyclosporin A treatment is only recommended for immune-mediated KCS and is contraindicated with other causes of KCS such as drug-induced or viral infections.

Another embodiment of the present invention relates to the administration of INF-α for purposes of enhancing saliva production in a patient having a disease state which results in abnormal mouth dryness, or xerostomia. In this embodiment, the IFN-α, is administered in a dosage form suitable to allow or promote the INF-α to contact the oral and pharyngeal mucosa, and the saliva producing cells (minor and major glands). Examples of such dosage forms are saliva miscible or saliva soluble dosage forms such as aqueous solutions and lozenges, respectively, and other art recognized dosage forms which allow or promote mucosal contact with the dose of interferon.

In another embodiment of the present invention, INF-α is administered to a patient suffering from pulmonary disease wherein the airways of said patient are becoming blocked with mucous, such as the pulmonary symptoms suffered by patients afflicted with cystic fibrosis. In this embodiment, INF-α can be administered in any manner appropriate to deliver an effective amount of INF-α to the patient; however, oral, buccal and particularly topical administration of INF-α by inhalation are efficient means of drug delivery for purposes of treating such pulmonary disorders in accordance with this invention. For inhalation administration, the types of inhaler that may be used in carrying out the present invention include metered dose inhalers, dry powder inhalers, nebulizers, aerosols, steam-carried formulations, and the like. Appropriate INF-α treatment dosages for all embodiments of the present invention range from about 0.1 IU/lb to about 100 IU/lb of patient body weight.

Thus in accordance with this embodiment of the present invention a patient with cystic fibrosis is treated with INF-α wherein the drug is administered as an aerosol mist or powder and inhaled by the patient. The IFN-α is optionally administered using a metered dose inhaler, whereby about 75 IU to about 1000 IU of IFN-α is delivered with each administration. The metered dose inhaler is configured such that a pressurized canister containing a propellant, an appropriate carrier compound and INF-α can be opened by depressing the top,, thus releasing the dose of INF-α in aerosol form into a mouthpiece through which the patient breathes. The dosage administration can be repeated as necessary to help facilitate clearing of the lungs and ease breathing.

In another embodiment of the present invention, IFN-α is used to treat patients afflicted with abnormal vaginal dryness. Any suitable dosage formulation which provides contact of INF-α with the vaginal mucosa can be used for the present method. Typically, INF-α is administered as a cream, ointment, suppository and the like.

Example 1

INF-α Augmentation of Transcription and Production of AQ-5 in Cultured Parotid Gland Tissue Two samples of normal human parotid gland tissue were removed during surgical extirpation of a Warthin's tumor (RB parotid) and during a parotid exploration for intraparotid lymphadenitis (JF parotid). Tissues were immediately placed in a small volume of RPMI-1640 containing 5% heat-inactivated AB+ human serum (v/v), glutamine (2 mM), penicillin (50 U/ml), gentamicin and streptomycin (50 µg/ml each) (RPMI+) and kept at 4° C. during transport to the laboratory. The RPMI-1640 was decanted, and tissue samples snap frozen in cryotubes by immersion in liquid nitrogen. The samples were then stored at −120° C. until use. Fifth passage human parotid gland (HS 917) was also obtained from American Type Culture Collection (ATCC) (Rockville, Md.), and tissue samples snap frozen in cryotubes and stored frozen at −120° C. until use.

Thawed tissue samples were teased apart, and approximately $5\times10^5$ cells distributed in 25 $cm^2$ flasks. Each flask was incubated for 5 minutes at 37° C. with 1.0 ml trypsin-EDTA (0.2% trypsin v/v, 1.0 mM ED TA). Five ml of RPMI+ per flask was then added, and preparations incubated at 37° C. in 5% $CO_2$ until a confluent cell growth was noted (generally overnight). The media was then decanted, and 5.0 ml of fresh RPMI+ containing 0, 100, 500, or 1,000 IU/ml INF-α added. Cultures were incubated at 37° C. in 5% $CO_2$ for an additional one, two or nine hours, the supernatants decanted, and the cells harvested for Reverse Transcriptase-PCR and Western Blot assays. All studies were done on first pass (RB and JF parotids) or sixth pass (HS 917 parotid) cultures.

To quantitate the level of transcription of the gene encoding the aquaporin protein, total cellular RNA was extracted from homogenized parotid tissue by the sequential addition of RNAzol™ B (Tel-Test, Inc., ° Friendswood, Tex.) (0.4 ml/1 $\times10^6$ BEC) and chloroform (0.2 ml/2.0 ml homogenate). The suspension was vortexed, placed on ice for 5 min, and centrifuged at 12,000g for 15 min at 4° C. The aqueous phase was washed twice with 0.4 ml phenol:chloroform (1:1, v/v), and once with 0.4 ml of chloroform, each time centrifuging the suspension at 12,000 g for 15 min at 4° C. RNA was precipitated with 0.1 volume 7.5 M ammonium acetate and ethanol on dry ice. After centrifugation at 12,000 g for 15 min at 4° C., the RNA pellet was washed with 70% ethanol. The RNA pellet was then dried under vacuum, and resuspended in 20–30 µl DEPC-treated water. Samples were further processed if the 260/280 nm optical density ratio was >1.8. RNA was quantitated by optical density readings at 260 nm, and with DipStick (Invitrogen, San Diego, Calif.). The integrity of the 28S and 18S bands was determined by electrophoresis in 2% ethidium bromide-stained agarose gels.

First-strand cDNA was synthesized using Reverse Transcription System Kit (Promega, Madison, Wis.) in the presence of Avian Myeloblastic Virus reverse transcriptase (1.0 U/µl), 1 mM each of dATP, dCTP, dGTP and dTTP, RNase inhibitor (1 U/µl), RT buffer (5 mM KCl, 10 mM Tris-HCl, pH 8.8, and 0.1% Trita x-100 (final concentration)), and $MgCl_2$ (5 mM), using oligo(dT) (0.5 µg/µg RNA) as a primer in a total volume of 20 µl. The preparation was incubated at 42° C. for 30 min, 99° C. for 5 min, and on ice for 5 min to complete the reverse transcription, and stored at −70° C. until used. Ten ug of total RNA was used in each cDNA synthesis reaction.

PCR amplification was done on aliquots of the cDNA in the presence of $MgCl_2$ (1.65 nmM), and paired AQ-5-specific and GADPH-specific primers (0.2 µM of each primer) in a total of 50 µl PCR SuperMix (GibcoBRL, Gaithersburg, Md.). For AQ-5 primers, two 20 mers, aagaccatggagctgaccac (left), and ccctctctaactgtgcagcc (right) oligos were designed based on the human AQ-5 cDNA sequence. PCR was done for 40, 50 or 60 cycles under the following conditions: initial denaturation at 95° C. for 2 min, denaturation at 94° C. for 45 sec, annealing at 60° C. for 45 sec, and extension at 72° C. for 90 sec. Final extension was at 72° C. for 10 min. Ten microliters of the amplified products were subjected to electrophoresis on a 2% agarose gel containing ethidium bromide. Care was taken to ensure equal RNA loading, and negative DNA controls were run with each experiment to exclude contamination or nonspecific amplification.

Identity of PCR products was determined by the sizes of the amplified fragments (174 bp for AQ-5 and 593 bp for GADPH) and, in the case of AQ-5, by nucleotide sequencing. For sequencing, the 174 bp band was excised from agarose gels, and the DNA purified using a GlassMax DNA Isolation Matrix System (GibcoBRL, Gaithersburg, Md.). Purified DNA was then sequenced using the above two oligos. The 174 bp sequence was compared with that of human AQ-5 cDNA using GenBank and the BLAST program, and showed a 95% identity with the human AQ-5 gene. Semi-quantitation was performed using an Alphalmager™ 2000 Digital Imaging System (Alpha Innotech Corp., San Leandro, Calif.) to calculate AQ-5/GADPH ratios.

Studies on the effects of INF-α on AQ-5 transcription using the method described above were done on 1 hour cultures of all three parotids, 2 hour cultures of RB and HS 917 parotids, and a 9 hour culture of RB parotid. AQ-5 was constitutively expressed in all three parotid glands, being detectable on RT-PCR after 60 amplifications.

IFN-α augmented AQ-5 transcription at all study times in each of the three parotid glands with peak effects occurring at one hour (Table 1—data expressed as mean±s.e.m.). The level of AQ-5 transcription was linearly related to the concentration of INF-α (FIG. 1).

TABLE 1

| | AQ-5 mRNA Level (% increase over baseline) | | |
|---|---|---|---|
| Culture Time (hrs) | With 100 IU/ml IFN-α | With 500 IU/ml IFN-α | With 1,000 IU/ml IFN-α |
| 1 (N = 3) | 65 ± 51 | 88 ± 47 | 167 ± 93 |
| 2 (N = 2) | 36 ± 10 | 93 | 111 ± 10 |
| 9 (N = 1) | — | 75 | 91 |

To determine whether INF-α treatment increased the amount of aquaporin protein expressed, Western Blotting techniques were used in which parotid tissue was homogenized in 8 M urea containing protease inhibitor mix (lmM each of antipain, aprotinin, bestatin, chromostatin, pepstatin A, leupeptin and PMSF), centrifuged at 13,000g for 10 minutes, and the supernatant collected. Protein samples were analyzed by SDS-PAGE, using the buffer system of Laeramli and gels of 10% acrylamide in a Bio-Rad Mini Gel System. Electroblotting of the SDS-PAGE separated polypeptides onto nitrocellulose membranes was carried out as described elsewhere. Nitrocellulose blots containing immobilized Isamples were reacted with affinity purified rabbit polyclonal antibody to AQ-5. The antibody was raised against a protein-linked synthesized peptide which corresponded to the C-terminal 25 amino acids of rat AQ-5, and is specific for both rat and human AQ-5 protein. The secondary antibody was horseradish peroxidase conjugated goat anti-rabbit IgG (Pierce, Rockford, Ill.). The bands were visualized using the SuperSignal Western 5 Blotting Kit (Pierce, Rockford, Ill.) and Fuji RX x-ray film, and quantitated using the AlphaImager 2000 Digital Imaging System.

Figure 2:
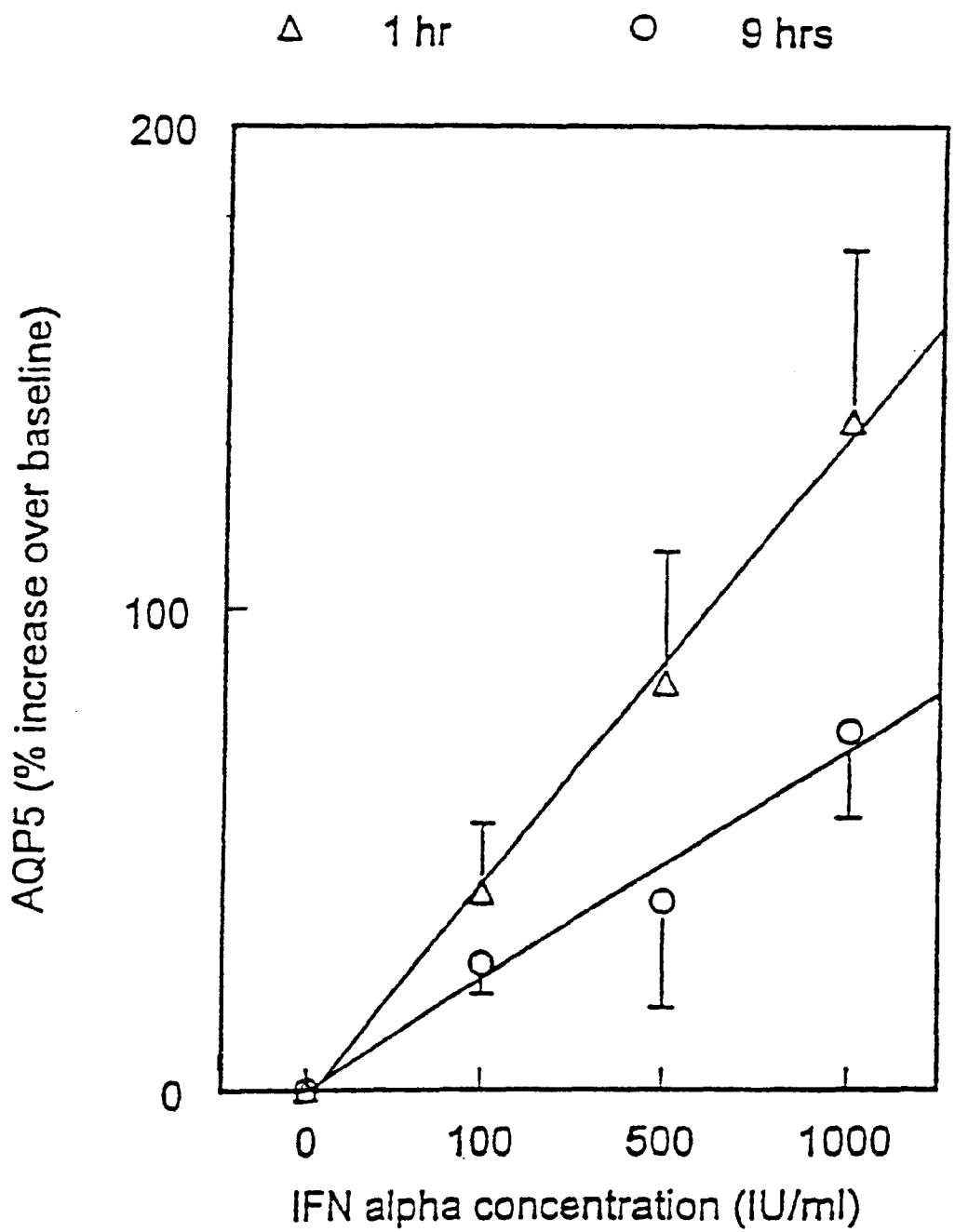
FIG. 2 is a graph showing the relationship between aquaporin-5 protein production and interferon-alpha concentration.

The Western blot studies described above were done on 1, 2 and 9 hour cultures of RB and HS 917 parotids, and on 1 and 2 hour cultures of JF parotid. IFN-α augmented AQ-5 protein production at all study times in each of the three parotid glands with peak effects occurring at one hour (Table 2-data expressed as mean ± s.e.m.). The level of AQ-5 protein production was linearly related to the concentration of INF-α at each of these incubation times (FIG. 2).

TABLE 2

| Culture Time (hrs) | AQ-5 Protein Level (% increase over baseline) | | |
|---|---|---|---|
| | With 100 IU/ml IFN-α | With 500 IU/ml IFN-α | With 1,000 IU/ml IFN-α |
| 1 (N = 3) | 42 ± 15 | 85 ± 27 | 138 ± 36 |
| 2 (N = 3) | 39 ± 16 | 67 ± 46 | 77 ± 26 |
| 9 (N = 2) | 27 ± 7 | 40 ± 23 | 75 ± 18 |

Example 2

Administration of INF-α to Dogs with Keratoconjunctivitis Sicca (KCS)

Dogs diagnosed with chronic (>3 months. in duration) KCS were selected for clinical trial. All dogs selected had normal physical examinations, complete blood counts, serum chemistry profile, and thyroid function. All ocular and systemic medication, except topical artificial tears, were discontinued at least 2 weeks prior to beginning the clinical trial. Dogs selected to be entered into this study demonstrated residual lacrimal function (>1 but <10 mm/minute Schimmer tear test (STT)). Oral INF-α was administered once daily to the dogs by their owners as the only therapy for KCS once the patients entered the trial.

Escalating doses of natural human recombinant INF-α were tested. Physical and ophthalmic examinations (biomicroscopy, indirect ophthalmoscopy) were performed every 2 weeks for the duration of the trial (84 days). These examinations included performing STT and assessing severity of the ocular inflammation. Each dog was given either two or three separate, escalating doses of the INF-α (20, 40, and 80 IU) to determine the most effective dose. The test product was packaged in 3 ml, low-density polyethylene, blow-mold single dose units containing 1 ml of INF-α. The test product was refrigerated (2–8° C. ) during storage and administered into the buccal cavity. The owners were instructed to withhold food or water for 5 minutes before and after treatment.

A favorable response to the INF-α included an increase of ≧5 mm/min on the STT and/or substantial improvement in clinical signs (e.g., decreased mucus discharge, blepharospasm, conjunctival hyperemia, etc) as observed by the owner or clinician. Whether or not the dogs responded to the 20 IU dose of INF-α, all dogs were placed on 40 IU of IFN-α after 4 weeks. At 8 weeks, "response" was again assessed; only dogs that did not respond to the 20 or 40 IU dose of INF-α were raised to 80 IU of INF-α. If the dog did not respond to any of the doses of the INF-α, then topical 0.2% cyclosporin A ointment was given to the dog (twice daily) and biweekly reevaluations were performed.

Twenty dogs with a diagnosis of KCS in one or both eyes were admitted into the study. Six dogs had unilateral and 14 had bilateral KCS. All dogs that were entered into the study were neutered, with 14 females and 6 males. The study group represented a variety of dog breeds including American cocker spaniels (n=6), Shih tzus (n=3), bulldogs (n=3), Beagles (n=2), Yorkshire terriers (n=2), a West Highland white terrier, a Siberian husky, a German shepherd dog, and a shar pei. The mean and median age of the dogs was 9.0±2.9 (mean±standard deviation) and 9 years, respectively. All dogs had chronic KCS of at least 3 months duration with a mean and median duration of 3.1±SD 2.6 and 2 years, respectively.

A favorable response was observed in 55% of all dogs treated (11/20). Clinical findings of those dogs that responded included increased wetting of the eyes, decreased mucus discharge, and fewer signs of discomfort.

Figure 3:
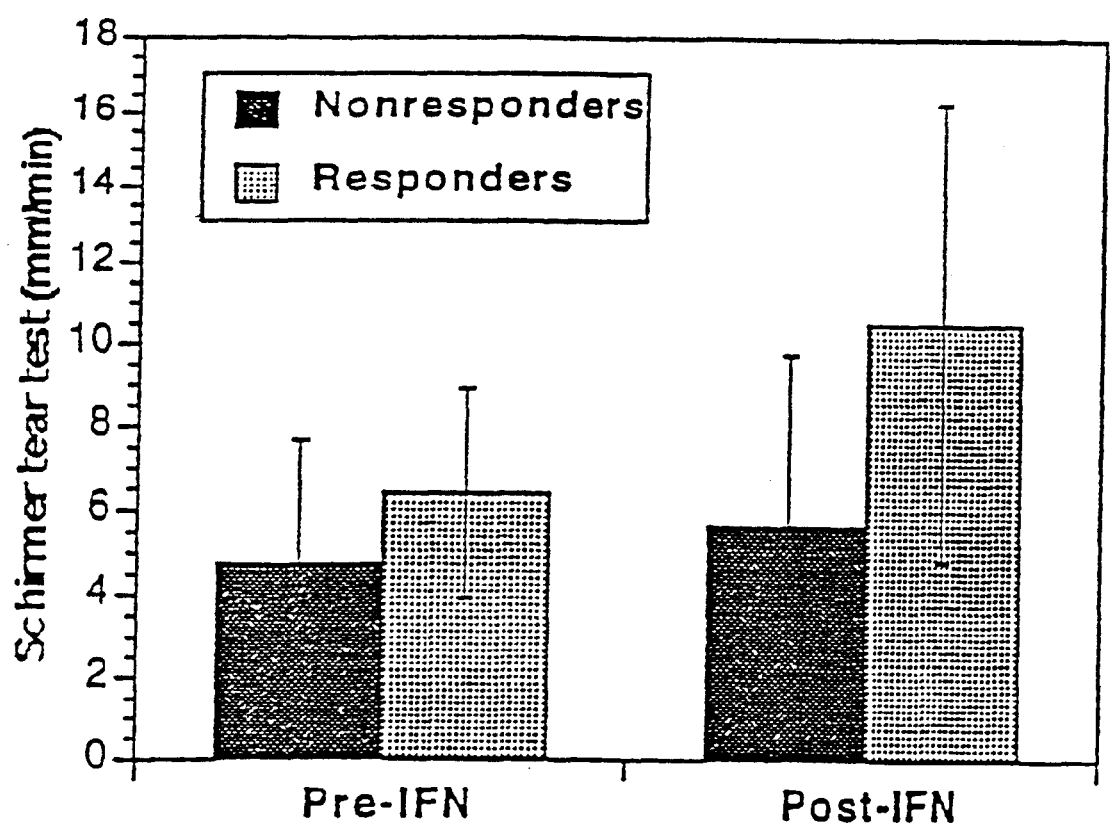
FIG. 3 is a bar graph showing the effect of interferon-alpha treatment on the Schimmer tear test.

There was no significant difference in pretreatment mean STT between the dogs that responded (6.4±SD 2.5 mm/min) to the oral INF-α and those that did not (4.7±2.9 mm/min) (FIG. 3). Seven of the eleven dogs with favorable outcome had an increased STT of 5 mm/min or greater, after treatment with oral INF-α. The dogs that did respond had a mean STT value (10.5±5.7 mm/min) that was significantly greater than their pretreatment STT and greater than the posttreatment mean STT (5.6±4.1 mmn/min) of dogs that did not respond (P<0.001) (FIG. 3).

All dogs that responded did so with the 20 or 40 IU dose of IFN-α. Of the 11 dogs that responded to INF-α treatment, 3 had responded after 14 days on 20 IU, 5 by 28 days on 20 IU, and 3 after 28 days on 40 IU (56 days after starting INF-α—28 days on 20 IU and 28 days on 40 IU). No additional dogs responded when placed on 80 IU.

No side effects were noticed and all dogs tolerated the treatment well. For the dogs that responded, the owners of the dogs were pleased with the ease of administration of the medication, the fact that no "eye medications" had to be given, and that the medication only had to be given once a day. For 4 animals that did not respond to any of the doses of INF-α, topical 0.2% cyclosporin A ointment was administered topically in both eyes twice a day. There was a slight increase (<5 mm/min) in STT in 2 of 4 dogs after 2 weeks on cyclosporin A.

Example 3

Administration of INF-α Lozenges for Increasing Saliva Production in HIV Patients Suffering from Xerostomia INF-α was diluted and mixed in pharmaceutical grade anhydrous crystalline maltose (ACM) and compressed into lozenges weighing 200 mg. Magnesium stearate was added as a lubricant/excipient. The dosage of IFN-α to be administered was three (3) 150 IU lozenges per day (450 IU daily dose). Subjects self-administered a lozenge containing 150 IU at each of 3 approximate times per day: 8 am, 2 pm and 8 pm. Each lozenge was held in the oral cavity, allowed to dissolve into the saliva and the saliva swished around the mouth before swallowing. Treatment was continued for a total of 12 weeks.

Effect assessments were based upon objective changes in salivary flow rates, and subjective changes in oral dryness as reported by the subjects. Changes in unstimulated whole saliva and stimulated whole saliva were the primary outcome variables for this study. The methods used to measure these variables were as follows:

(1) Unstimulated Whole Saliva (UWS) was collected using the "spitting method" as described by Navazesh. *Annals of New York Academy of Sciences*, 694:72–77, 1993. The subject tipped his/her head slightly forward with the lower jaw relaxed, allowed the saliva to pool in the mouth for 60 seconds, and then spit the saliva into a pre-weighed collector. This was repeated 4 times for a total of 5 minutes of collection time. At the end of the collection, the amount of saliva was determined by weight;

(2) Stimulated Whole Saliva (SWS) was performed by having the subject first swallow any accumulated saliva in the mouth. The subject then placed an unflavored, unsweetened piece of chewing gum base into the mouth and chewed at a rate of 60 chews per minute. The speed of chewing was standardized with the use of a metronome. The subject spit out the accumulated saliva after each minute of chewing for a total of five minutes. At the end of the collection, the amount of saliva was determined by weight.

(3) Subjective reports of changes in oral dryness were assessed by 100-mm visual analog scales and other questionnaires.

The results of the study are summarized in Table 3 for nine participants.

TABLE 3

| Subject ID# | Final Visit | Change in SWS | Change in UWS | Change (mm) in Oral Dryness* |
|---|---|---|---|---|
| 001 | Week 12 | −21% | 2% | 53 |
| 002 | Week 12 | 6% | 313% | 7 |
| 003 | Week 4 | 19% | 2% | 39 |
| 004 | Week 12 | 46% | 87% | 70 |
| 005 | Week 4 | 89% | 8% | 31 |
| 008 | Week 2 | 37% | 37% | ND |
| 009 | Week 4 | 87% | 65% | 16 |
| 010 | Week 12 | −38% | −36% | 29 |
| 011 | Week 12 | 67% | −24% | 38 |

*An increase indicates improvement.

SWS=Stimulated Whole Saliva; UWS=Unstimulated Whole Saliva.

A 50% increase is considered clinically significant for both stimulated whole saliva (SWS) and unstimulated whole saliva (UWS). Three of nine (33%) subjects had a positive response for either SWS or UWS, but only one subject had a positive response for both. Six of eight (75%) subjects had a clinically significant (>25mm) increase in the visual analog scale for oral dryness.

We claim:

1. A method of improving pulmonary function in a patient suffering from a pulmonary disorder characterized by mucous blocked airways, said method comprising the step of administering interferon-alpha in an amount effective to upregulate aquaporin protein expression in lung cells and enhance mucous mobilization.

2. The method of claim 1 wherein the interferon is administered orally.

3. The method of claim 1 wherein the interferon is administered bucally.

4. The method of claim 1 wherein the interferon is administered topically to the lung cells by inhalation.

5. The method of claim 1 wherein the effective amount of interferon-alpha is from about 0.1 IU/lb to about 100 IU/lb of patient body weight.

6. The method of claim 4 wherein the interferon is administered using a metered dose inhaler.

7. The method of claim 6 wherein a metered dose from the metered dose inhaler is from about 75 IU to about 1000 IU of interferon.

* * * * *